(12) United States Patent
Ganey et al.

(10) Patent No.: US 9,522,507 B2
(45) Date of Patent: Dec. 20, 2016

(54) METHOD AND DEVICE FOR PRODUCING SHEET MATERIAL

(75) Inventors: Timothy Ganey, Tampa, FL (US); Jörg Meisel, Berlin (DE)

(73) Assignee: SPINPLANT GMBH, Leipzig (DE)

( * ) Notice: Subject to any disclaimer, the term of this patent is extended or adjusted under 35 U.S.C. 154(b) by 812 days.

(21) Appl. No.: 13/989,391

(22) PCT Filed: Nov. 23, 2011

(86) PCT No.: PCT/EP2011/070870
§ 371 (c)(1),
(2), (4) Date: Jun. 14, 2013

(87) PCT Pub. No.: WO2012/069558
PCT Pub. Date: May 31, 2012

(65) Prior Publication Data
US 2014/0051317 A1    Feb. 20, 2014

(30) Foreign Application Priority Data
Nov. 24, 2010   (EP) .................................. 10192393

(51) Int. Cl.
*D01D 13/00*  (2006.01)
*D01D 13/02*  (2006.01)
(Continued)

(52) U.S. Cl.
CPC .............. *B29D 7/01* (2013.01); *A61L 27/24* (2013.01); *A61L 27/365* (2013.01); *A61L 27/54* (2013.01);
(Continued)

(58) Field of Classification Search
CPC ... B29C 47/0076; B29C 47/065; D01D 5/003; D01D 5/0038; D01D 5/0061; D01D 5/0076; D01D 5/0092; D01D 13/00; D01D 13/02; D04H 1/728; D04H 3/02; D04H 3/03
(Continued)

(56) References Cited

U.S. PATENT DOCUMENTS

2012/0040581 A1   2/2012 Kim

FOREIGN PATENT DOCUMENTS

| JP | 2006-283241 A | 10/2006 |
|---|---|---|
| WO | 2006/052039 A1 | 5/2006 |

(Continued)

OTHER PUBLICATIONS

N. J. Garrahan et al., A new method for the two-dimensional analysis of bone structure in human iliac crest biopsies, Journal of Microscopy, vol. 142, Issue 3, pp. 341-349, Jun. 1986.

*Primary Examiner* — Leo B Tentoni
(74) *Attorney, Agent, or Firm* — Maschoff Brennan

(57) ABSTRACT

A method for producing a sheet material is disclosed, comprising the steps of providing a carrier material solution comprising a carrier material, and depositing the carrier material onto a collector by electrospinning the carrier material solution out of a spinning device, the collector having a first electrical polarity and the spinning device having a second electrical polarity being opposite to the first polarity. The collector comprises at least one differential section, the electrical polarity of which is adjusted during deposition of the carrier material in such a manner that it either resembles the electrical polarity of the remaining sections of the collector or differs from it. The invention further relates to a device for carrying out said method and a sheet material which can be produced by said method.

9 Claims, 2 Drawing Sheets

(51) Int. Cl.

| | | |
|---|---|---|
| *D04H 3/02* | (2006.01) | |
| *D04H 3/03* | (2012.01) | |
| *B29D 7/01* | (2006.01) | |
| *B29C 47/00* | (2006.01) | |
| *B29C 47/06* | (2006.01) | |
| *D01D 5/00* | (2006.01) | |
| *A61L 27/24* | (2006.01) | |
| *A61L 27/36* | (2006.01) | |
| *A61L 27/54* | (2006.01) | |
| *A61L 27/56* | (2006.01) | |
| *A61L 27/58* | (2006.01) | |
| *D01F 1/10* | (2006.01) | |
| *D04H 1/728* | (2012.01) | |
| *D04H 3/016* | (2012.01) | |

(52) U.S. Cl.
CPC ............... *A61L 27/56* (2013.01); *A61L 27/58* (2013.01); *B29C 47/0076* (2013.01); *B29C 47/065* (2013.01); *D01D 5/0038* (2013.01); *D01D 5/0076* (2013.01); *D01D 5/0092* (2013.01); *D01F 1/10* (2013.01); *D04H 1/728* (2013.01); *D04H 3/016* (2013.01); *Y10T 442/681* (2015.04)

(58) Field of Classification Search
USPC .... 264/10, 464, 465, 466, 484; 425/174.8 R, 425/174.8 E, 377, 382.2
See application file for complete search history.

(56) References Cited

FOREIGN PATENT DOCUMENTS

| WO | 2009/049563 A2 | 4/2009 |
| WO | 2010/041944 A1 | 4/2010 |
| WO | 2010/112564 A1 | 10/2010 |

METHOD AND DEVICE FOR PRODUCING SHEET MATERIAL

CROSS-REFERENCE TO A RELATED APPLICATION

This application is a National Phase Patent Application of International Patent Application Number PCT/EP 2011/070870, filed on Nov. 23, 2011, which claims priority of European Patent Application Number 10 192393.6, filed on Nov. 24, 2010.

BACKGROUND

The invention relates in an aspect to a method for producing a sheet material, in another aspect to a device for carrying out such a method and in another aspect to a sheet material which can be obtained by such a Sheet materials produced by common electrospinning methods exhibit an essentially non structured, planar surface. This is due to the fact that all material is deposited onto a uniform carrier during the electrospinning method. Such a method in an according device is for example known from WO 2009/049563 A2.

SUMMARY

It is an object of the invention to provide a method by which it is possible to produce sheet materials having a structured surface as well as providing an according device for carrying out said method, and a sheet material which can be obtained by such a method.

This object is achieved by a method having the features explained in the following. Such a method for producing sheet material comprises the following steps. First, a carrier material solution comprising a carrier material is provided. Second, the carrier material is deposited onto a collector by electrospinning the carrier material solution out of a spinning device. Thereby, the collector has a first electrical polarity and the spinning device has a second electrical polarity being opposite to the first polarity. According to an aspect of the invention, the collector comprises at least one differential section, the electrical polarity of which is adjusted during the deposition of the carrier material in such a manner that it either resembles the electrical polarity of the remaining sections of the collector or differs from it.

The collector may be for example a cord or a belt of varying width to meet standard sizing in manufacturing efficiency. Suited belts may have a width in the range of 15 to 50 cm, in particular of 20 to 40 cm, in particular of 25 to 35 or to 30 cm. The length of the belt may be in the range of 80 cm to 1.50 m, in particular of 90 cm to 1.40 m, in particular of 1 m to 1.30 m, in particular of 1.10 to 1.20 m.

In an embodiment, exactly one spinning device is allocated to exactly one collector. This means, the collector only collects material being spun from the single spinning device.

The spinning device may be a nozzle through which the carrier material solution can be sprayed, or a turning (or rotating) pin located in a bath of the carrier material solution. By turning or rotating the pin in the bath, the carrier material solution is transported out of the bath and accelerated in the direction of the collector.

In a further embodiment, the carrier material is solved or dispersed in at least one liquid chosen from the group of water, alcohols like methanol or ethanol, aqueous solutions of acids or bases like acetic acid or sodium hydroxide and organic solvents like acetone or 1,1,1,3,3,3-hexaflouoro-2-propanol to produce a carrier material solution.

The term "carrier material solution" also encompasses "carrier material dispersions". This means, it is not necessary that the carrier material is ideally solved in an according liquid. If an essentially stable dispersion of the carrier material in an according liquid is established, electrospinning can also take place.

In an embodiment, the polarity of the spinning device is positive and that of the collector is negative. This means that the spinning device acts as an anode and the collector as a cathode or ground. In an embodiment, the differential section would then have also a positive polarity so that it can also be denoted as differential anode.

In an embodiment, the electrospinning may be performed at a voltage of 8 to 20 kV, in particular of 10 to 17 kV, in particular of 12 to 15 kV between the collector and the spinning device. A voltage of approximately 12.5 kV is particularly suited. Those voltages are well suited for accelerating the carrier material solution sufficiently fast out of the spinning device towards the collector. Further electrospinning parameters like the speed of a rotating pin for ejecting some of the carrier material solution out of a reservoir of the carrier material solution or the flow rate of the carrier material solution towards a nozzle, and the distance between the spinning device and the collector can be adjusted to the respective needs according to standard protocols of electrospinning.

In an embodiment, the collector is moved during the deposition of the carrier material with respect to the spinning device, wherein the position of the differential section remains constant with respect to the spinning device. A movement of the collector can for example be achieved in designing the collector as an endless belt which is always moved in one direction. The differential section does not move with the rest of the belt but remains constant with respect to the spinning device. In other words, the differential section is not a certain physical portion of the belt itself, rather all sections of the belt can be the differential section whenever they are in a certain position with respect to the spinning device.

The movement of the collector may for example be in the range of some millimeters per minute.

In a further embodiment, the collector comprises a plurality of differential sections, the polarity of which is individually adjusted during deposition. By this embodiment, it is possible to produce a certain deposition pattern of the material to be deposited on the collector by adjusting the polarity of the individual differential sections in a time-dependent manner.

In a further embodiment, the collector is moved with respect to the spinning device during deposition of the carrier material in order to deposit at least two layers of carrier material above each other. In doing so, the collector may be moved more than twice over the spinning device to achieve deposition of more than two layers on the collector. Generally, the number of layers deposited on the collector is determined by the number of (repetitive) arrangements of the collector in a certain position at that site at which material from the spinning device is accelerated towards the collector.

The differential section of the collector is located in the area in which material being provided from the spinning device is usually deposited on the collector. If the differential section has the same polarity as the spinning device, no material will be deposited in the area of the differential section, but only in the other areas of the collector which have a polarity being opposite to that of the spinning device and being reached by the material ejected from the spinning device. Thereby, it is possible to produce a pattern of voids within the material deposited on the collector.

In a further embodiment, the polarity of the differential section is adjusted in a time-dependent manner such that the deposition pattern of the carrier material is the same in at least two adjacent layers of carrier material deposited on the collector. Thereby, it is possible to produce a three-dimensional structure in the deposited material. By adjusting the polarity of the differential section such that all deposited layers show the same structured pattern, the three-dimensional surface structure of the produced sheet material resembles the two-dimensional polarity pattern of the differential section being present at a distinct time point and therewith at a distinct position of the collector with respect to the spinning device.

In other words, the polarity of the differential section is changed in an embodiment in a time-dependent manner such that the deposited material comprises voids forming a three-dimensional structure of the deposited material. This means, a real structure pattern can be formed by defining voids within the material to be deposited on the collector. Dependent on the number and the size of the differential sections used, the size and number of the voids and therefore the structure of the deposited material can be adjusted to the individual needs.

In a further embodiment, the carrier material is collagen, a mixture of collagen and hydroxy apatite, gelatin, alginates, chitosan, silk, cellulose, polyurethane, a polyester, polycaprolactone, polylactide, polypyrrole, polyaniline, polyacetylene, polythiophene, a copolymer of the preceding polymers and/or a copolymer bearing carboxylic acid groups and/or amine groups.

Further suited carrier materials are amino acid structures like oligopeptides or polypeptides. Oligopeptides are considered to consist of a sequence of up to 10 amino acids, whereas polypeptides are considered to be amino acid structures having more than 10 amino acids. Proteins are to be considered to be encompassed by the term “polypeptide”. This means the amino acids structure can exhibit a primary, secondary and tertiary structure by itself so that the structure of the material to be deposited on the collector can exhibit an individually adjusted sub-structure. By using an amino acid structure, one can take advantage not only of the secondary or tertiary structure of the oligopeptides or polypeptides, but also of the amphiphilic charge of the single amino acids being present in the oligopeptides or polypeptides.

Well-suited collagens are collagen type I, II, III, V, or XI, wherein type I collagen is particularly well suited. The collagen might for example have a human, bovine, equine, ovine or fish origin or can be an artificial collagen resembling human, bovine, equine, ovine or fish collagen, or might consist of collagen, or collagen fibrils that have been expressed in culture by vector incorporation without limitation to mammalian source.

In a further embodiment, the carrier material solution further comprises at least one auxiliary substance. This auxiliary substance is chosen from the group consisting of osteoinductive substances, electrically conductive substances, electrically semiconductive substances, electrically insulating substances, antibacterial substances, antiviral substances, antifungal substances, ceramics (like, e.g., hydroxyapatite ceramics), barium, bromine, copper, niobium, lithium, germanium, titanium, lead, zirconium, silicon, silver, zinc, polyurethane, silver hydrogen sulfate, gallium orthophosphate ($GaPO_4$), langasite ($La_3Ga_5SiO_{14}$), barium titanate ($BaTiO_3$), lead titanate ($PbTiO_3$), lead zirconate titanate ($Pb[Zr_xTi_{1-x}]O_3$ $0<x<1$), potassium niobate ($KNbO_3$), lithium niobate ($LiNbO_3$), lithium tantalate ($LiTaO_3$), sodium tungstate ($Na_2WO_3$), $Ba_2NaNb_5O_5$ and $Pb_2KNb_5O_{15}$.

The auxiliary substance can be entrapped within the polymer network of the carrier material or the carrier material and a crosslinker, respectively. Particularly, the auxiliary substance is chemically and/or physically bound to the carrier material. The entrapment offers the effect that a certain placement/precipitation of the auxiliary substance can be achieved, e.g. a placement/precipitation in the banding structure of the carrier material perpendicular to scaffold orientation. Thus, if hydroxyapatite is used as auxiliary substance and collagen is used as carrier material, the natural orientation of hydroxyapatite with respect to collagen in normal bone (i.e. in the banding structure of bone perpendicular to scaffold orientation) can be mimicked.

In a further embodiment, the crosslinker is nordihydroguaiaretic acid (NDGA). The structure of NDGA is the following:

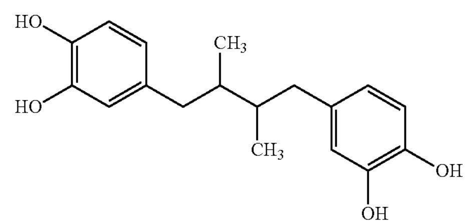 [SMILES: CC(Cc1ccc(O)c(O)c1)C(C)Cc1ccc(O)c(O)c1]

It turned out that NDGA is a very well suited crosslinker for crosslinking the polymer of the carrier material. Nanofibers of the carrier material being crosslinked by NDGA show a very high stability and are very long-lasting in solutions in which non-crosslinked polymers already dissolve. NDGA forms a polymer into which the carrier material is embedded. The NDGA admixture gives surface tension and attachment of the final material, enables the broad dimension of underformed bone which accentuates the tensile component of undermodeled bone, and enables the isotrophic structure of underloaded, non-directed compressive modeling to load.

In a further embodiment, the electrospun carrier material is washed after having been removed from the collector. By washing, remainders of non-reacted crosslinker or reaction co-products can be removed, thus improving the biocompatibility of the obtained product. Washing can be performed by an aqueous solution of an alcohol like for example ethanol in a concentration of for example 80%, 70%, 60% or 50% (v/v). Further suited washing solutions are low salt buffers like phosphate buffered saline (PBS). Washing can be performed in a two-step manner by first using an alcoholic solution and afterwards a low salt buffer (or first a low salt buffer and afterwards an alcoholic solution) as washing solutions.

In an alternative embodiment, no washing step is necessary due to the specific crosslinker chosen and the concentration in which it is used.

The object is further achieved by a device having the characteristics explained in the following. Such a device is suited for carrying out a method according to the preceding explanations. It comprises a spinning device, a collector and a first high voltage power supply connected to the spinning device and to the collector and being provided and arranged to polarize the spinning device and the collector with opposite electrical polarities. According to an aspect of the invention, the collector comprises at least one differential section, the electrical polarity of which can be adjusted in such a manner that it either resembles the electrical polarity of the remaining sections of the collector or differs from it.

The electric polarity of the differential section might be provided by the first high voltage power supply or by a second high voltage power supply being independent on the first high voltage power supply.

In an embodiment, the electrical polarity of the differential section is mediated by at least one differential electrode contacting the collector. These differential electrodes might be made of any electrically conductive material such as a metal. Copper is a very well suited metal for the production of the differential anode since it exhibits a good conductivity and can be easily handled.

In a further embodiment, a plurality of differential electrodes is used, wherein each individual differential electrode is a tooth of a comb. Alternatively, each individual differential electrode might represent a punctate connection to a high voltage power supply. "Punctate" in this circumstance means not necessarily that the cross-section of the individual differential electrodes has to be angular. Rather, cross-sections of the individual differential electrodes having other shapes (like e.g. rectangular or quadratic) are also encompassed by the term "punctate".

By using a plurality of differential electrodes, the areas of interest (e.g. the areas in which material shall be deposited) can be very well separated from exclusions (e.g. areas in which no material deposition is wanted). When the individual differential electrodes are designed as a plurality of teeth of a comb, the single teeth of the comb are, in an embodiment, electrical insulated from each other so that each individual differential electrode can be controlled independently from the other individual differential electrodes. It is also possible to combine a sub-set of a certain number of individual differential electrodes which are not insulated from each other and which are controlled as a group. A group-wise control of the differential electrodes can thus be made possible.

In a further embodiment, each individual differential electrode has an area in the range of 100 to 10 000 $\mu m^2$ for contacting the collector. This area might be identical to the area of the cross-section of the differential electrode. Other suited lower limits for this area are 200, 500, 1 000 and 2 000 $\mu m^2$ and suited upper limits for this area are 9 000, 8 000, 7 000, 6 000, 5 000, 4 000 and 3 000 $\mu m^2$, wherein any combinations of the lower and upper limit are within the scope of an embodiment of this invention.

The electrodes might for example have a rectangular cross-section of 50 $\mu m \times 50$ $\mu m$, thus leading to an area of 2 500 $\mu m^2$. The space between single individual differential electrodes might be in the range of 10 to 100 $\mu m$, in particular of 20 to 90 $\mu m$, in particular of 30 to 80 $\mu m$, in particular of 40 to 70 $\mu m$, in particular of 50 to 60 $\mu m$.

The object is further achieved by a sheet material having the features explained in the following. Such a sheet material has a three-dimensional surface structure for enabling tissue growth. It is in particular obtainable by a method according to the above explanations. The sheet material comprises voids and struts surrounding the voids, wherein the struts are made of a carrier material being built up from nanofibers having a diameter of less than 1 200 nm. According to an aspect of the invention, the struts have a thickness in the range of 100 to 600 $\mu m$, wherein the average distance between the edges of two adjacent struts is in the range of 200 to 750 $\mu m$. In an embodiment, the nanofibers might have a diameter of less than 1 100 nm, in particular less than 1 000 nm, in particular less than 900 nm, in particular less than 800 nm, in particular less than 700 nm, in particular less than 600 nm, in particular less than 500 nm, in particular less than 400 nm, in particular less than 300 nm. The thickness of the struts might lie in an embodiment in the range of 130 to 550 $\mu m$, in particular of 200 to 500 $\mu m$, in particular of 230 to 450 $\mu m$, in particular of 300 to 400 $\mu m$. The average distance might in an embodiment be in the range of 300 to 600 $\mu m$, in particular of 400 to 500 $\mu m$.

The arrangement of voids and struts builds up the three-dimensional surface structure of the sheet material. The specific ratio between voids and struts enables tissue growth on the sheet material in a very good manner. This is due to the fact that the ratio of voids and struts as well as the thickness and the distance between adjacent struts is chosen in such a manner that the structure of the sheet material resembles a specific three-dimensional surface structure of the tissue to be grown on the sheet material. To be more exact, the morphology of the material surface is fashioned with respect to, and is mimetically inspired to represent that morphology that tissue exhibits which is exposed to reduced gravity and afterwards becomes responsive and sensitive to normal gravity. Especially, if bone is used as tissue to be grown on the sheet material, such a three-dimensional surface structure mimicking the morphology of bone after gravity change, enhances the tissue growth performance on the sheet material. The structure of the claimed sheet material also resembles the structure of understimulated osteoporetic bone.

In an embodiment, the distribution of struts and voids resembles the distribution of trabeculae and spaces between trabeculae in bone of an organism who was subjected to reduced gravity and returned to normal gravity. In an embodiment, the status of the bone of the organism obtained within 1 day to 6 months, in particular 3 days to 5 months, in particular 1 week to 4 months, in particular 2 weeks to 3 months, in particular 1 month to 2 months after return to normal gravity is used as comparative template. In an embodiment, the organism has been subjected to reduced gravity over a period of at least 1 week, in particular at least 1 month, in particular 2 months to 24 months, in particular 3 months to 18 months, in particular 4 months to 12 months, in particular 6 months to 9 months. Reduced gravity is for example present outside the atmosphere of the earth (i.e. in an altitude of 100 km or more above the ground). Normal gravity is present on the ground of earth.

In other words, the distribution of struts and voids in the sheet material is, in an embodiment, a model of biogeometric heterotrophism. In an embodiment, it exhibits a fractal geometry to inherent shifting of an gravitational influence (or lack thereof) that cannot be assigned to digitial, or finite element analysis. In a further embodiment, the distribution resembles an analog geotrophism.

In an embodiment, the ratio of material volume to strut volume is in the rage of 15 to 30, in particular of 17 to 25. Thus, there are many voids present in the overall material, leading to a high porosity of the material The nanofibers building up the sheet material might be essentially aligned to each other in one direction. Alternatively, the fibers can be randomly orientated, or stacked matters of fibers can bear respective orthogonal relationships with adjacent levels.

In an embodiment, the average cross-sectional area of a single void is in the range of 2 000 to 100 000 $\mu m^2$. Such a range is suited for a cell to adhere to the material surrounding an according void. The average cross-sectional area of a single void might also be in the range of 5 000 to 75 000 µm², in particular of 10 000 to 60 000 µm², in particular of 20 000 to 50 000 µm², in particular of 30 000 to 40 000 µm².

In an embodiment, the distribution of the voids or pores is not too regular in order to produce a material which reflects the irregularity of natural tissue. For example, smaller voids might be located next to larger voids so that the material strength increases as compared to material in which distinct areas of large voids and distinct areas of small voids exist.

Although voids or pores in natural tissue, in particular in bone, show an orientation reflecting the overall orientation of the tissue, i.e. pores in bone are longer in the longitudinal direction of bone than in the transversal direction of bone, such a general orientation of the sheet material is not achieved in an embodiment. By randomly distributed voids in the produced sheet material, no preferred direction of the sheet material has to be considered when this material is implanted during an operation into a body of a patient.

In a further embodiment, the voids or material recesses have an average depth in the range of 10 to 100 µm, in particular of 20 to 90 µm, in particular of 30 to 80 µm, in particular of 40 to 70 µm, in particular of 65 to 75 µm, in particular of 50 to 60 µm. The depth is measured from a virtual surface covering the topmost layer of nanofibers of the carrier material. Thus, the depth indicates how far the void or material recess reaches into the sheet material from the topmost layer of nanofibers of the material. The average depth is chosen such that cells can easily attach to the material surrounding the voids in order to promote tissue growth.

In an embodiment, the sheet material exhibits an maximum tensile strength of ca. 50 to 200 MPa, in particular of ca. 75 to 175 MPa, in particular of ca. 90 to 150 MPa, in particular of ca. 100 to 125 MPa.

In a further embodiment, the sheet material exhibits an elastic modulus of ca. 300 to 700 MPa, in particular of ca. 350 to 650 MPa, in particular of ca. 400 to 600 MPa, in particular of ca. 450 to 580 MPa, in particular of ca. 500 to 550 MPa.

The sheet material described above can be used as template for tissue growth both for in vitro and in vivo applications. The cells to be grown can be mesenchymal stem cells, fully competent stem cells, expanded somatic lineages, separated and suspended cells, peripheral circulating cells and cells of either included or induced potential. In vivo cell growth can be for example achieved with respect to bone growth or with respect to healing processes of wounds. For example, the sheet material can be implanted into a body of a patient (either human or animal) and act as (temporary) bone substitute material. If it is made from a biodegradable or bioresorbable material like for example collagen, the sheet material will be resorbed or degraded over time and newly grown bone will replace the sheet material step by step. By promoting bone growth due to the specific structure of the sheet material, healing processes after operations are accelerated. The use of a sheet material as described above for enabling tissue growth either in vivo or in vitro is also part of an aspect of the invention. Specifically, the use of a sheet material as described above as bone substitute material is encompassed by an aspect of the invention. The sheet material may embody itself with charge that potentiates tissue differentiation. Stem cell differentiation has been closely tied to electrovolt membrane potential during phenotypic emergence. Electrospinning, charge potentiation, and multi-laminar sheet formation all carry the option to defined physical conditions of the matrix, and define voltage differences in regenerative tissues. Processed materials from electrospun biologic components, both linear and in piled matte, will be used to define matrix charge and enliven the differentiation process.

Further embodiments explained with respect to the claimed method can also be applied in an analogous way to the claimed device or the claimed sheet material and are not repeated here for the sake of brevity only.

BRIEF DESCRIPTION OF THE DRAWINGS

Aspects of the invention are further explained in more detail by the description of the figures.

DETAILED DESCRIPTION

Figure 1:
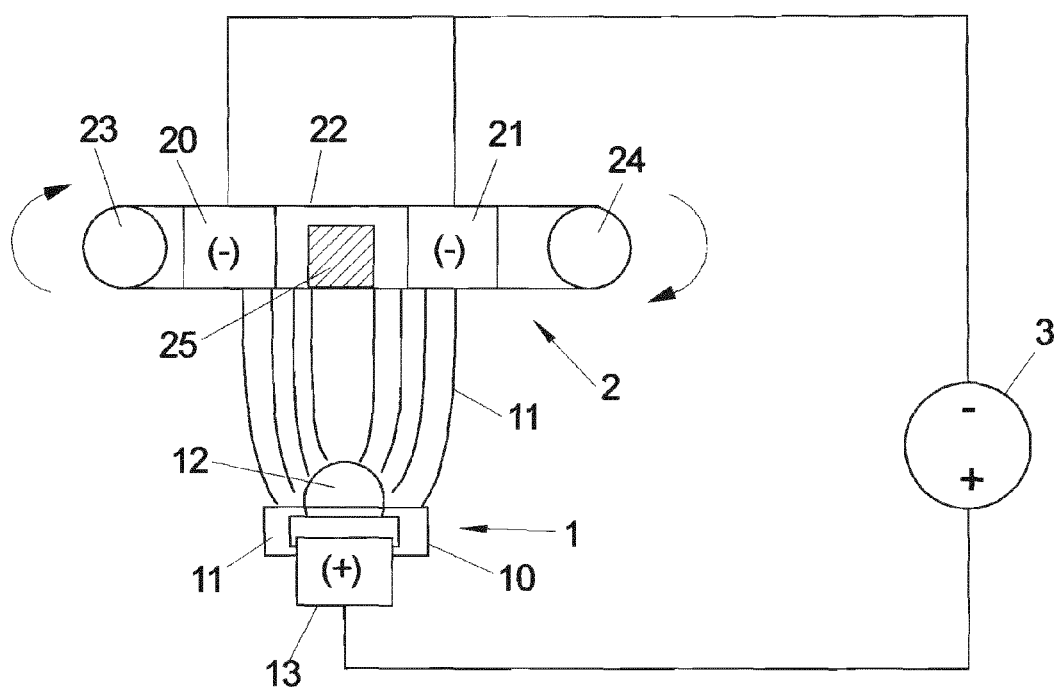
FIG. 1 shows a schematic depiction of an electrospinning device comprising a differential section.

In FIG. 1, an electrospinning apparatus comprising a spinning device 1 and a collector device 2 is shown. This spinning device 1 consists of a container 10, which is filled with a collagen solution 11 as carrier material solution and a rotating pin 12, by the rotation of which the collagen solution 11 is thrown out of the container 10 towards the collector device 2. The spinning device 1 further comprises a first electrode 13 which is connected to a first high voltage power supply 3. This first high voltage high power supply 3 is also connected to a second electrode 20 and a third electrode 21 being located in the interior of an endless belt 22 being movably mounted around a first roller 23 and a second roller 24 and forming part of the collector device 2. The belt 22 is the actual collector of the collector device 2. Two arrows indicate the movement of the belt 22 around the first roller 23 and the second roller 24 in operation of the electrospinning device.

Between the second electrode 20 and the third electrode 21, a differential area 25 is located. Within the differential area 25, one or more differential sections are present (cf. FIG. 3). To simplify matters, in the following the term "differential area" is used as synonym for "differential section" since not all differential sections can be depicted in the schematic representation of the Figures. It should be kept in mind that the polarity of the whole differential area 25 needs not necessarily the same since the individual differential sections might exhibit different polarities. To explain the general principle, this is, however, not of primary importance.

This differential area 25 comprises at least one differential electrode, the polarity of which can be adjusted independently on the first electrode 13, the second electrode 20 and the third electrode 21. Particularly, the polarity of the differential area 25 or each differential section within it can be adjusted to match the polarity of the first electrode 13. In this case, the collagen solution 11 being electrospun from the spinning device 1 towards the collector 2 will only be deposited on those sections of the belt 22 which have—due to the influence of the second electrode 20 and the third electrode 21—a negative polarity. Since the differential area 25 has the same polarity like the spun collagen solution 11, no material deposition will take place within the differential area 25. Only when the differential area 25 is brought to a negative polarity matching the polarities of the remaining sections of the belt 22, the material deposition of the collagen solution 11 will also take place within the differential area 25. Thus, by adjusting the polarity of the differential area 25, it is possible to allow a material deposition in this area or to inhibit it.

It is obvious from FIG. 1 that the position of the differential area 25 remains constant with respect to the spinning device 1, but not with respect to the moving belt 22. This means that all sections of the belt 22 moving over the differential area 25 will exhibit the same polarity like the electrode of the differential area 25. Therefore, depending on the current position of an individual section of the belt 22, it might either have a negative polarity (due to the second electrode 20 and the third electrode 21) or a positive polarity (due to the differential area 25 and its according electrode, as far as this electrode currently exhibits a positive polarity).

By moving the belt 22 several rounds around the rollers 23 and 24 and time-dependently adjusting the polarity of the differential area 25, it is possible to allow a collagen deposition on certain sections of the belt 22, but inhibit it on other sections of the belt 22. It should be noted that the dimensions of the differential area 25 and the area in which a material deposition can generally take place due to the spinning of the rotating pin 12 as shown in FIG. 1 do not represent the real dimensions. Rather, the material deposition can generally take place only within a very small space. The spinning device ejects the collagen solution 11 such that it reaches a certain belt section in any case before this belt section has reached the second electrode 20. If the collagen is really deposited onto the belt 22 depends on the polarity of the belt 22. The distance between the differential area 25 and the second electrode 20 as well as the third electrode 21 is adjusted such that the belt 22 remains its polarity given by the electrode in the differential area 25 until it reaches the second electrode 20.

This will become even clearer from the explanations of the next Figures.

Figure 2:
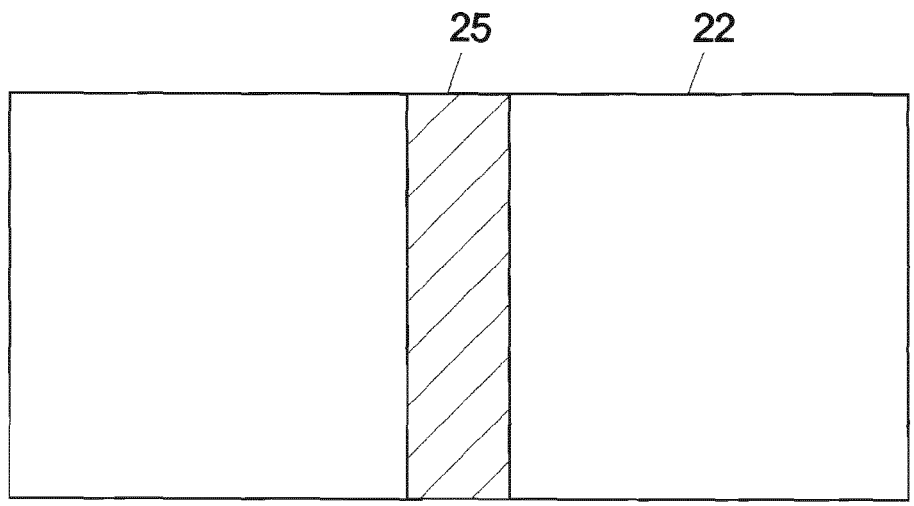
FIG. 2 shows a schematic depiction of a collector of an electrospinning device, the collector comprising a differential section.

FIG. 2 shows a schematic depiction of the bottom of the belt 22 of FIG. 1 comprising the differential area 25. The differential area 25 has a length which corresponds to the width of the belt 22. In other embodiments, it might be slightly less than the width of the belt 22.

Figure 3:
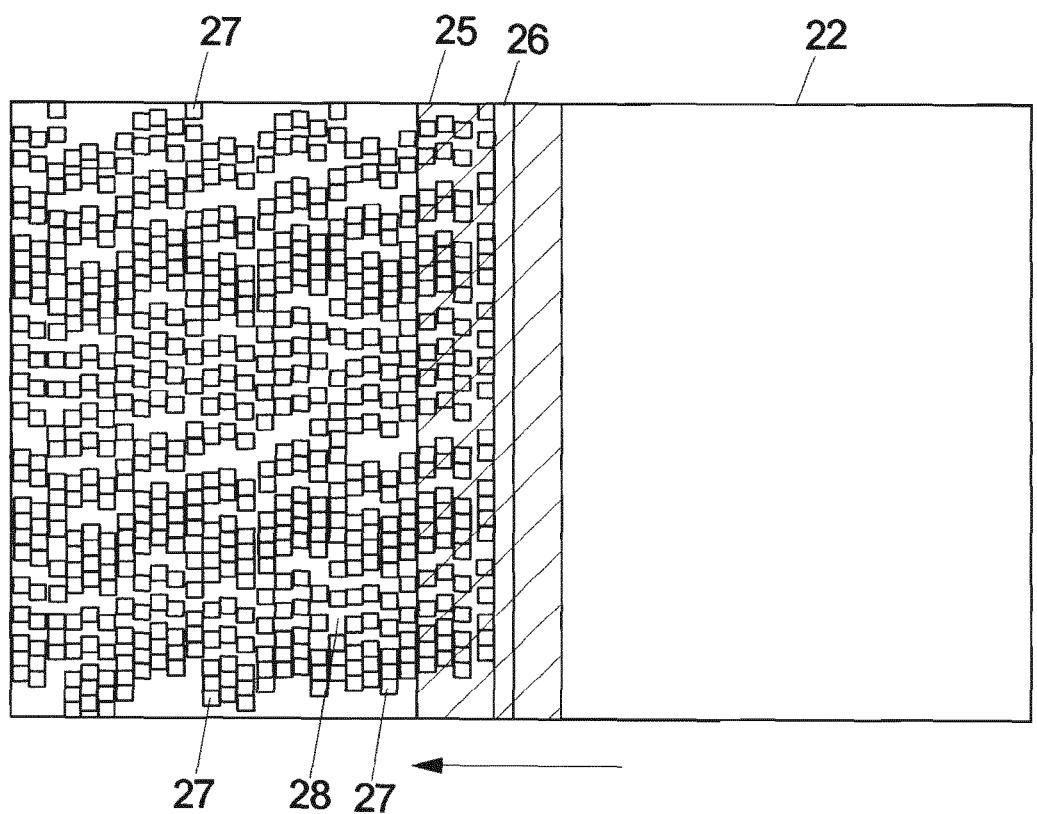
FIG. 3 shows a schematic depiction of a material pattern deposited on a collector of a electrospinning device, the collector comprising a differential section.

In FIG. 3, a targeted material deposition is shown which is achieved when the spinning device of FIG. 1 is in operation. The view to the belt 22 is the same as in FIG. 2, i.e. towards the bottom of the belt 22. An arrow indicates the belt travel during operation. Within the differential area 25, a comb 26 is located which consists of a plurality of individual differential electrodes which are not shown for the sake of clarity. Each individual differential electrode of comb 26 can be separately controlled so that the polarity of each individual differential electrode can be adjusted according to the needs. Whenever a single individual differential electrode has a negative polarity (i.e. the same polarity like the remaining sections of the belt 22), a material deposition at this section of the belt 22 is possible. The deposited material 27 is indicated in FIG. 3 as white squares. The quadratic shape of the deposited material 27 reflects the quadratic cross-section of the individual differential electrodes of comb 26. Whenever an individual differential electrode has the same polarity like the first electrode 13 of the spinning device 1 (i.e. a positive polarity), no material deposition will take place at the according section of the belt 22. Thereby, voids 28 can be introduced into the deposited material 27.

It should be noted that a material deposition can only be inhibited within an area of the belt 22, in which the belt 22 still has its positive polarity given by the individual differential electrodes of differential area 25. With respect to FIG. 3, this means that the spinning device 1 is located such that generally no material deposition onto the belt 22 takes place on the right side of comb 26. On the left side of comb 26, material deposition takes place on all sections of the belt 22 which are negatively charged. However, material deposition is inhibited within an area being sufficiently close enough to comb 26 so that a positive polarity brought onto a distinct section of the belt 22 by an individual differential electrode of comb 26 is still present on that section and is not reversed by grounding the belt 22 in total again by the second electrode 20 (cf. also FIG. 1).

Usually, it can be assumed that the belt 22 will not loose its polarity given by an individual differential electrode within the differential area 25 until this section of the belt 22 reaches the second electrode 20. Therefore, the space between the differential area 25 and the second electrode 20 has to be adjusted with respect to the distance between the bottom of the belt 22 and the spinning device 1 because this distance determines (together with other parameters like the velocity of the rotating pin 12 and the belt travel) the general distance of material deposition on the belt 22.

The invention claimed is:

1. A method for producing a sheet material, comprising the following steps:
   providing a carrier material solution comprising a carrier material, and
   depositing the carrier material onto a collector by electrospinning the carrier material solution out of a spinning device, the collector having a first electrical polarity and the spinning device having a second electrical polarity being opposite to the first polarity,
   wherein
   the collector comprises at least one differential section, the electrical polarity of which is adjusted during deposition of the carrier material in such a manner that it either resembles the electrical polarity of the remaining sections of the collector or differs from it.

2. The method according to claim 1, wherein the collector is moved during deposition of the carrier material with respect to the spinning device, wherein the position of the differential section remains constant with respect to the spinning device.

3. The method according to claim 1, wherein the collector comprises a plurality of differential sections, the polarity of which is individually adjusted during deposition.

4. The method according to claim 1, wherein the collector is moved with respect to the spinning device during deposition of the carrier material in order to deposit at least two layers of carrier material above each other.

5. The method according to claim 4, wherein the polarity of the differential section is time-dependently adjusted in such a manner that the deposition pattern of the carrier material is the same in at least two adjacent layers of carrier material deposited on the collector.

6. The method according to claim 1, wherein the polarity of the differential section is changed in a time-dependent manner such that the deposited material comprises voids forming a three-dimensional structure of the deposited material.

7. The method according to claim 1, wherein the carrier material comprises one or more of the group of collagen, a mixture of collagen and hydroxy apatite, gelatin, alginates, chitosan, silk, cellulose, polyurethane, a polyester, polycaprolactone, polylactide, polypyrrole, polyaniline, polyacetylene, polythiophene, a copolymer of the preceding polymers, a copolymer bearing carboxylic acid groups and/or amine groups, oligopeptides and polypeptides.

8. The method according to claim 1, wherein the carrier material solution further comprises at least one auxiliary substance of the group consisting of osteoinductive substances, electrically conductive substances, electrically semiconductive substances, electrically insulating substances, antibacterial substances, antiviral substances, antifungal substances, ceramics, barium, bromine, copper, niobium, lithium, germanium, titanium, lead, zirconium, silicon, silver, zinc, polyurethane, silver hydrogen sulfate, gallium orthophosphate, langasite, barium titanate, lead titanate, lead zirconate titanate, potassium niobate, lithium niobate, lithium tantalate, sodium tungstate, $Ba_2NaNb_5O_5$ and $Pb_2KNb_5O_{15}$.

9. A device for carrying out the method according to claim 1, comprising
a spinning device,
a collector and
a first high voltage power supply connected to the spinning device and to the collector and being provided and arranged to polarize the spinning device and the collector with opposite electrical polarities,
wherein:
  the collector comprises at least one differential section, the electrical polarity of which is adjusted in such a manner that it either resembles the electrical polarity of the remaining sections of the collector or differs from it,
  the electric polarity of the differential section is mediated by at least one differential electrode contacting the collector,
  a plurality of differential electrodes is used, each individual differential electrode being the tooth of a comb, and
  each individual differential electrode has an area in the range of 100 to 10,000 $\mu m^2$ for contacting the collector.

* * * * *